(12) United States Patent
Hilgendorf et al.

(10) Patent No.: US 6,203,502 B1
(45) Date of Patent: Mar. 20, 2001

(54) RESPIRATORY FUNCTION MONITOR

(75) Inventors: Edwin J. Hilgendorf, West Bend; Son Duc Tran; Steven P. Pruzina, both of Milwaukee; Mark Storsved, Menomonee Falls, all of WI (US)

(73) Assignee: Pryon Corporation, Menomonee Falls, WI (US)

( * ) Notice: Subject to any disclaimer, the term of this patent is extended or adjusted under 35 U.S.C. 154(b) by 0 days.

(21) Appl. No.: 09/049,166

(22) Filed: Mar. 27, 1998

(Under 37 CFR 1.47)

Related U.S. Application Data

(60) Provisional application No. 60/042,212, filed on Mar. 31, 1997.

(51) Int. Cl.[7] .................................................. A61N 5/00
(52) U.S. Cl. .................. 600/538; 600/532; 128/200.11; 128/207.29; 73/1.02; 73/1.07
(58) Field of Search .................. 128/200.11, 207.29; 73/1.02–1.07; 600/528–541

(56) References Cited

U.S. PATENT DOCUMENTS

| | | |
|---|---|---|
| 3,380,298 | 4/1968 | Hanson . |
| 3,924,612 | 12/1975 | Dempster et al. . |
| 4,345,463 | 8/1982 | Wilson et al. . |
| 4,581,945 | 4/1986 | Rusz . |
| 4,959,990 | 10/1990 | Morris . |
| 5,038,773 | 8/1991 | Norlien et al. . |
| 5,088,332 | 2/1992 | Merilainen et al. . |
| 5,111,827 | 5/1992 | Rantala . |
| 5,197,895 | 3/1993 | Stupecky . |
| 5,347,843 | 9/1994 | Orr et al. . |
| 5,379,650 | 1/1995 | Kofoed et al. . |
| 5,710,370 | 1/1998 | Shanahan et al. . |
| B1 4,154,100 | 11/1987 | Harbaugh et al. . |

*Primary Examiner*—Cary O'Connor
*Assistant Examiner*—Michael Astorino
(74) *Attorney, Agent, or Firm*—Ryan Kromholz & Manion, S.C.

(57) ABSTRACT

A respiratory function monitoring device comprising a flow sensor and a conversion device is herein disclosed. Also disclosed are structures for carrying out an auto-zero calibration, a purging function, and temperature compensation. Methods for implementing the auto-zero calibration, the purge function, and the temperature compensation are also disclosed.

11 Claims, 8 Drawing Sheets

RESPIRATORY FUNCTION MONITOR

This application claims benefit to Provisional Application Ser. No. 60/042,212, and filing date Mar. 31, 1997.

BACKGROUND OF THE INVENTION

The present invention relates generally to the field of medical devices and specifically to medical devices which are designed to monitor the respiratory characteristics of patient breathing, especially those patients attached to mechanical ventilation systems. Persons who have suffered traumatic injury or some debilitating disease may have to be placed on mechanical ventilation systems. When a patient is on such a system it is for a doctor or other medical professional to gather data to assess whether a patent is able to breathe without the aid of the mechanical ventilation device. Monitoring of a patient's respiratory characteristics while the patient is connected to a mechanical ventilation system can be accomplished through the use of pulmonary mechanics techniques.

The term pulmonary mechanics refers to the graphical monitoring of a patient's lung and breathing performance. Pressure values corresponding to the ambient pressure in a patient's airways and to the volumetric flow of respiratory gases between the patient and a mechanical ventilator are measure and recorded. These values are then used to calculate and graphically display pulmonary mechanics parameters that assist the doctor or respiratory therapist in assessing, for example, a patient's pulmonary compliance, tidal volume, and work of breathing. This type of monitoring helps a doctor or respiratory therapist assess the patient's respiratory condition so that the ability of a doctor or other medical professional to intervene prior to the onset of respiratory fatigue or failure is improved.

In addition, this type of monitoring is very useful in making fine adjustments to a mechanical ventilating system in order to optimize a patients ventilation. Pulmonary mechanics monitoring is also very useful in assessing whether and how a patient might be weaned from a mechanical ventilation system.

Prior to this invention there have been many different types of technologies utilized to accomplish respiratory monitoring. The most prevalent technology is use of a differential pressure flow meter. Differential pressure flow meters function by measuring a pressure drop across a restriction placed in an airway. This pressure drop is related to the flow rate of respiratory gases flowing through the airway in which the obstruction is placed. Using empirical methods a relationship can easily be established between the drop in pressure across a restriction in an airway and the amount of flow through that airway. Combining the flow rate through an airway with the ambient pressure within that airway allows a doctor or respiratory therapist to quickly assess a patient's ability to breathe on their own or to assess the performance of a ventilation system.

While respiratory monitoring systems in use in hospitals today are generally able to perform adequately, they are relatively large, complex, expensive to manufacture, sensitive to temperature fluctuations, and prone to quantization errors. Because the primary function of any mechanical ventilation system is to provide respiratory gases to a patient, all restrictions to flow of respiratory gases in the ventilation system must be minimized. This results in the need to use differential pressure type flow sensors that also minimize any restrictions to flow. But because the magnitude of a differential pressure signal is directly proportional to the magnitude of the flow restriction used in the differential pressure flow sensor, the situation arises where a relatively large range of flow rates within the ventilation system will produce a correspondingly small range of differential pressure signals. Where the analog-to-digital converter (A/D) used to convert analog signals from a differential pressure transducer to complimentary digital values has a limited dynamic range, quantization error will be introduced into the data stream of the differential pressure flow meter. Quantization error is defined in this context as an error relating to the assignment, by an A/D, of one digital voltage value to two distinct analog voltage signals representing different flow rates within the ventilation system's airways.

In attempting to remedy this quantization error some prior art devices created complicated variable gain systems to variably amplify voltage signals representative of flow rates within a ventilation system in such a way as to overcome the limited dynamic range of the A/ID converts available. However, these variable gain systems require numerous signal amplifiers making them harder to manufacture and ultimately increasing the end cost of the devices. Using a greater number of amplifiers also increases the possible amount of error in the device's output due to amplifier offset and gain differences.

Another problem associated with differential pressure type flow sensors is that of error introduced into the system due to temperature changes. Because pressure sensing devices such as a differential pressure transducer are sensitive to temperature in addition to pressure, any change in the temperature of the pressure transducer itself can cause critical variances in the resulting data. Even in temperature compensated transducer models, residual variations can cause unacceptable variances in the data.

Therefore there is a need for a respiratory function monitoring device that reduces or eliminates quantitisation errors over its useful range. A further need is recognized for a respiration monitoring device capable of calculating pulmonary mechanics parameters in a manner that is independent of any variations in temperature. Yet another need recognized is for an electronics package capable of performing pulmonary mechanics respiratory monitoring that is small, inexpensive and useable in a wide range of existing monitoring platforms including hand-held monitors and bedside cart-mounted monitors.

Therefore, it is an object of this invention to provide a flow sensor that has a low resistance to air flow therethrough and which also provides a more linear differential pressure output in response to low air flow rates.

It is another object of this invention to provide a wave form analyzing device capable of transducing the pressure signals derived from a flow sensor that has a high resolution output having little or no quantization error.

It is yet another object of this invention to provide a wave form analyzing device capable of transducing the pressure signals derived from a flow sensor that is immune from temperature induced drift in the output of the pressure transducers used to transduce the pressure signals from the flow sensor.

It is yet another object of this invention to provide a structure for purging the fluidic connections between the flow sensor and the wave form analyzer of blockages and foreign materials.

A final object of this invention is to provide methods for implementing an auto zero function and a purging function as well as for calibrating the wave form analyzing device and the flow sensor.

The present invention is an improvement on the above noted technology. The inventors know of no prior art that teaches or discloses the subject matter of the invention as claimed and described herein.

SUMMARY OF THE INVENTION

The present invention is most easily described as a respiratory function monitoring device comprising a flow sensing device that is fluidically coupled to a conversion device capable of transducing pressure signals transmitted from the flow sensing device. The flow sensing device is also known as a flow sensor. The flow sensing device is further comprised of a hollow cylindrical body having a bore with a first end and a second end. The first and second ends of the bore are arranged for connection between a ventilator and a patient. A strut is disposed within the bore of the body across the entire diameter of the bore and parallel to the axis of symmetry of the bore. The strut has symmetrical end portions that flow aerodynamically from a center portion and each of the symmetrical end portions has a leading edge with a groove formed therein. A pair of lumens are coupled to the outer surface of the body of the flow sensing device. Each of the lumens communicates with a respective groove so as to permit the measurement, across the strut, of a differential pressure of a gas flowing through the flow sensing device. The grooves formed into the leading edges of the end portions extend across substantially the entire height of the strut.

The conversion device is also known as a wave form analyzing device or as a wave form analyzer. The conversion device includes two differential pressure transducers. A first transducer is arranged to measure a differential pressure corresponding to a gas flow rate of the respiration gases flowing through the flow sensing device. A second transducer is arranged to measure a static pressure within the flow sensing device. The transducers are connected to amplifying means for amplifying voltage signals output by the pressure transducers. An analog to digital converter translates the analog voltage valves derived from the transducers into digital voltage values. A central processing unit communicates with the analog to digital converter and is capable of executing a program designed to convert the digital voltage values from the transducers into flow rate data and pressure data. An input/output means for communicating flow rate and pressure data to a host system is also provided. It should be pointed out that it is important that the analog to digital converter have at least four input channels.

An alternate embodiment of the present invention comprises the addition of a third transducer arranged to receive pressure signals from an esophageal pressure sensing device. The voltage signals of the third transducer are amplified by the amplifying means and translated by the analog to digital converter into digital voltage data which is processed by the central processing unit into pressure data that is transferred to the host system.

Another alternate embodiment of the present invention comprises the addition of a temperature indicating means arranged so as to give the temperature of the conversion device. This temperature indicating means is used to compensate for variations in the output of the transducers of the conversion device due to variations in the temperature of the conversion device.

In order to purge blockages and foreign materials from the means used to connect the flow sensing device and the transducers of the conversion device, the present invention may be provided with a purge system. The purge system comprises a first valve means, a second valve means, a third valve means and an air pump. The air pump has an inlet and an outlet, with the outlet of the air pump coupled by a first and second fluidic connection means to the first valve means and the second valve means, respectively. The third valve means is coupled to a first lumen of the flow sensing device via a third fluidic connection means and to a first input port of a flow transducer via a fourth fluidic connection means. The third valve means selectively permits communication between the first lumen and the first input port. The second valve means is coupled to a second lumen of the flow sensing device through a fifth fluidic connection means and to a second input port of the flow transducer via a sixth fluidic connection means. The first valve means is also coupled by a seventh fluidic connection means to the third fluidic connection means adjacent to the third valve means between the third valve means and the first lumen. An eighth fluidic connection means couples the second and third valve means such that the second and third valve means may selectively permit communication between the first input port and the second input port. The valve means of the purge system comprise solenoid activated three-way air valves and the fluidic connection means are comprised of discrete tubes. Alternatively, fluidic connection means may comprise channels formed within a solid valve manifold, the solid valve manifold being further arranged to receive the valve means.

A method of calibrating the flow rate output of the respiratory function monitoring device comprises the steps of characterizing a differential pressure response of the flow sensing device to a plurality of known flow rates, the characterization taking the form of a polynomial equation of at least second order; characterizing a voltage response of the transducer arranged to measure differential pressures within the flow sensing device to a plurality of known static pressures, the characterization taking the form of a polynomial equation of at least second order, the characterization taking into account a normal operating voltage of the transducer measuring the differential pressure; and combining the differential pressure response equation with the voltage response equation, the resulting equation being used by the processing means to calculate a flow rate using differential pressure data derived from the flow sensing device.

More specifically, the calibration of the differential pressure response of the flow sensing device comprises the steps of forcing gases through the flow sensor at known flow rates; recording the magnitudes of the known flow rates and the resulting pressure differentials present within the flow sensing device corresponding to each known flow rate; and characterizing the differential pressure response of the flow sensing device using the flow rate and pressure differential data. Characterizing the voltage response of the transducer arranged to measure differential pressures within the flow sensing device begins with connecting a static pressure source to a first and second input port of the transducer, the static pressure source being also connected to a means for measuring the magnitude of the pressure of the pressure source that is applied to the first and second input ports. A static pressure is applied to the first and second input ports of the pressure transducer and the magnitude of the pressure applied to the input ports is recorded. A voltage output by the pressure transducer corresponding to the applied pressure is also recorded. The pressure applied to the input ports of the transducer is then reduced to approximately nil and the actual pressure applied to the input ports along with the resulting voltage output by the transducer is recorded. The pressure source is next disconnected from the first and second input ports of the pressure transducer. The pressure source is reconnected to each of the first and second input ports of the pressure transducer, in turn and independently, and a pressure is applied to each of the input ports, again in turn and independently. The respective pressures applied to each of the first and second input ports and the corresponding voltages output by the pressure transducer are recorded. The pressure applied to the first and second input ports of the pressure transducer is again reduced, in turn and independently, to approximately nil and the actual pressure applied to the first and second input ports along with the resulting voltage output by the pressure transducer is recorded. Finally, the voltage response of the pressure transducer to the various static pressures is characterized using a polynomial equation of first order or above.

When the temperature indicating means is included as part of the conversion device, the calibration of the transducer arranged to measure differential pressures within the flow sensing device further comprises the steps of repeating the application of static pressures to the first and second input ports of the transducer, together and independently, at a first temperature and a second temperature. It is contemplated that the first temperature will be substantially equal to the desired operating temperature of the respiratory function monitoring device, i.e. approximately 25° C., and the second temperature will be between five and twenty degrees Celsius higher than the first temperature. The voltage response of the transducer is then characterized with respect to temperature and pressure.

Temperature, among other things, can cause the voltages output by a differential pressure transducer to drift. A method of compensating for drift in a flow transducer of a respiratory function monitor comprises the steps of calibrating the flow transducer to obtain a baseline offset voltage as part of a characteristic calibration function, periodically equalizing the pressure applied to the input ports of the flow transducer, recording an offset voltage corresponding to the application of equalized pressures to each of the first and second input ports of the flow transducer, comparing the baseline and recorded offset voltages to determine the difference therebetween, if any, and incorporating the respective differences between the baseline and recorded offset voltages into the characteristic calibration functions.

An alternate method of compensating for drift in the flow transducer of a respiratory function monitor, the method comprises the steps of calibrating the flow transducer to obtain a baseline offset voltage as part of a characteristic calibration function, periodically equalizing the pressure applied to the input ports of the flow transducer, recording a predetermined number of offset voltages corresponding to the application of equal pressures to each of the first and second input ports of the flow transducer, determining the differences, if any, between the baseline and recorded offset voltages, characterizing the variation between the baseline and recorded offset voltages over time using a polynomial function of at least the second order so as to permit the extrapolation of future offset voltages, and periodically recording additional offset voltage values and updating the characterization of the variation between the baseline and offset voltage values.

In order to minimize the disruption of the flow of pulmonary function data, the recordation of the offset voltages is instituted during periods of substantially no respiratory flow within the respiratory function monitor, preferably following the end of a patient's expiration.

It may also be necessary to periodically purge blockages and foreign materials from the fluidic connections between the flow sensor and the wave form analyzer. Generally speaking, the pulmonary function monitoring device comprises a flow sensing device and a conversion device, the flow sensing device being in fluidic communication with the conversion device via a plurality of fluidic connection means. The fluidic communication means themselves comprise a first tube connected between a first lumen of the flow sensing device and a first input port of a pressure transducer and a second tube connecting a second lumen of the flow sensing device to a second input port of the pressure transducer. A valve means is associated with the first and second tubes and provides a fluidic connection between the first and second tubes and an air pump. A method of purging this respiratory function monitor comprises the steps of periodically actuating the valve means to connect the air pump to the first and second tubes and activating the air pump to pump air through the tubes. It is preferred to actuate the valve means so as to independently connect each of the tubes to the air pump. Further, it is preferred to institute the purging of the tubes during periods of substantially no respiratory flow within the flow sensing device. In order to ensure that all foreign materials have been forced from the tubes, the air pump is activated for a period of time that is directly proportional to the frequency and magnitude of a pressure cycle caused by inspiration and expiration of a patient to which the respiratory function monitor is attached. Alternatively, the air pump can be activated for a predetermined amount of time or the air pump can be activated so as to pump a predetermined amount of air through the respective tubes.

DESCRIPTION OF THE DRAWINGS

FIG. 6B is a sectional view of the valve manifold taken along lines A—A of FIG. 6A.

FIG. 6C is a sectional view of the valve manifold taken along lines B—B of FIG. 6A.

FIG. 6D is a sectional view of the valve manifold taken along lines C—C of FIG. 6A.

DETAILED DESCRIPTION

Figure 1:
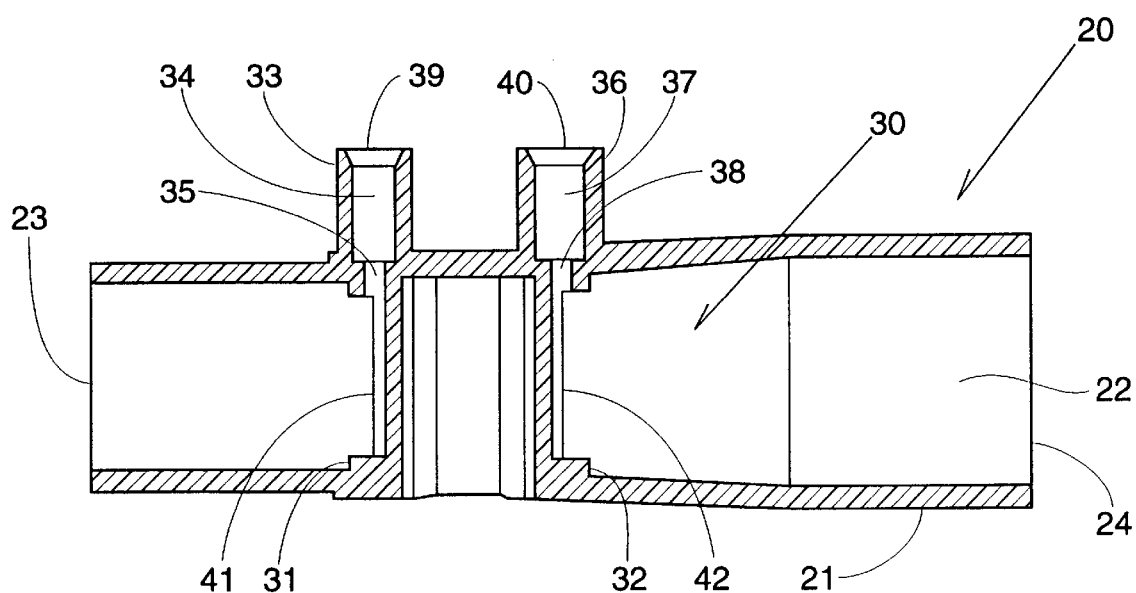
FIG. 1 is a longitudinal sectional view of the flow sensor.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims. Furthermore, as there are numerous embodiments of the present invention, to avoid confusion like elements will be labeled with like reference numerals.

Figure 3:
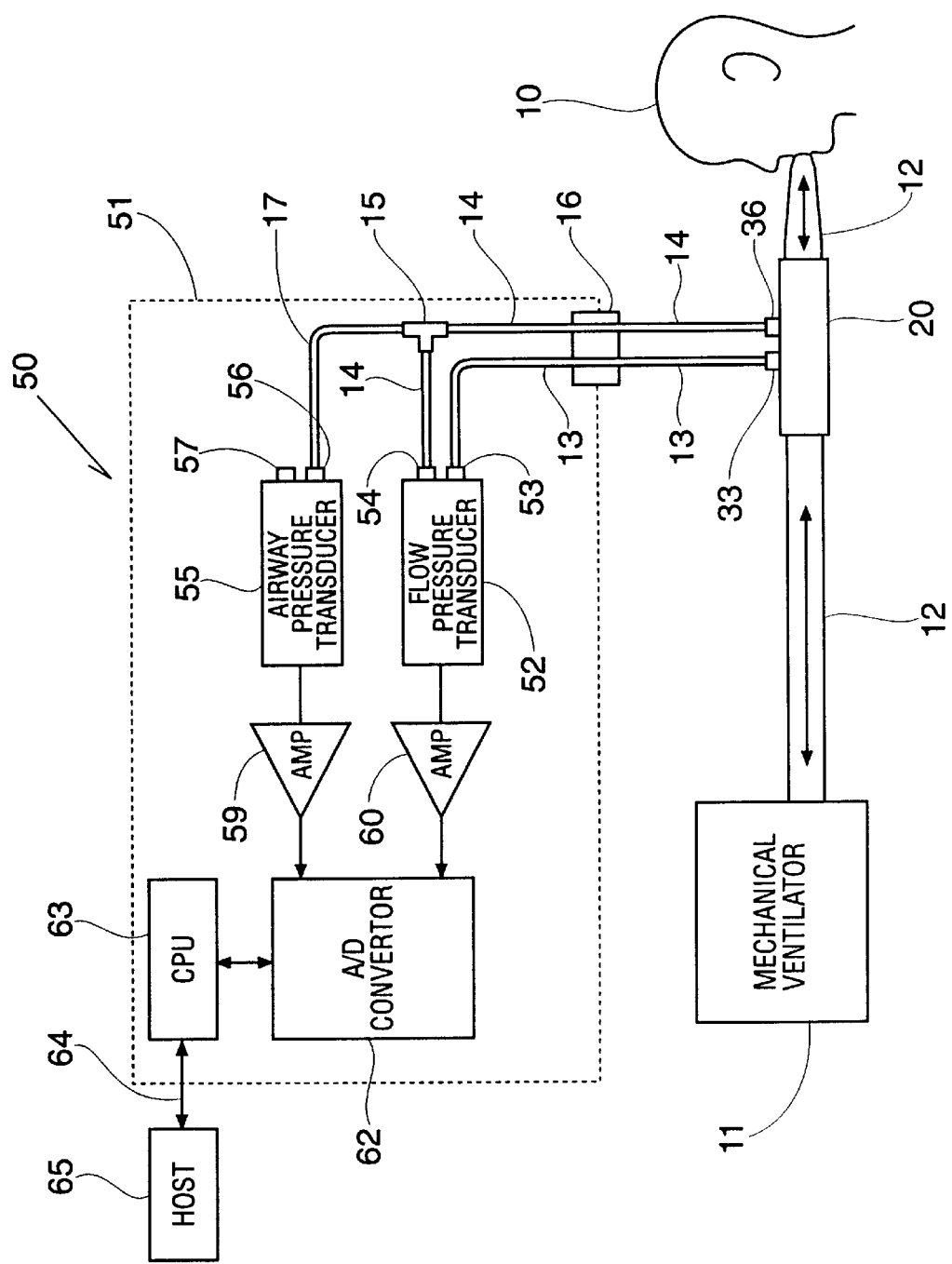
FIG. 3 is a schematic view of an alternate embodiment of the respiratory function monitoring device.

The reader's attention is directed to FIG. 3, which illustrates a basic respiratory function monitoring system that is comprised of a flow sensor 20 that is connected between a patient 10 and a mechanical ventilator 11 by tubing 12. The flow sensor 20 communicates pressure signals, via a plurality of lengths of standard plastic tubing 13 and 14, to a wave form analyzing device 50 that transduces the pressure signals into useful pulmonary mechanics data. A releasable connector 16 may be provided to permit the use of disposable flow sensors 20 with the wave form analyzing device 50. The wave form analyzing device 50 is comprised of a circuit board 51 upon which are mounted differential pressure transducers 52 and 55; amplifiers 59 and 60 for amplifying the signals from the differential pressure transducers 52 and 55, respectively; an analog to digital converter means 62 for converting the analog voltage values from the transducers 52, 55 into digital values; a central processing unit 63 for running a data filtering and conversion program; and an input/output means 64. As is well-known in the art, the central processing unit 63 is comprised of a microprocessor that operates in conjunction with a read-only memory means and a random-access memory means. The wave form analyzing device 50, via the input/output means 64, is in communication with a host system 65 that provides power for the wave form analyzing device 50 and also provides means for viewing the data output by the wave form analyzing device 50. The host system 65 may be a hand-held computer, a cart-mounted computer device, or a stand alone PC.

The flow sensor 20, illustrated in FIG. 1, is capable of generating differential pressure signals that are proportional to the flow rate of the respiratory gases that pass therethrough. The sensor 20 has a first end 23 and a second end 24 that are arranged in a typical male-female connection fashion that permits the flow sensor 20 to be quickly and easily connected in-line with the ventilator tubing 12 connecting a patient 10 to a mechanical ventilator 11. In the embodiment of FIG. 1 the first end 23 is shown as being the "male" portion and the second end 24 is shown as the "female" portion.

Figure 2:
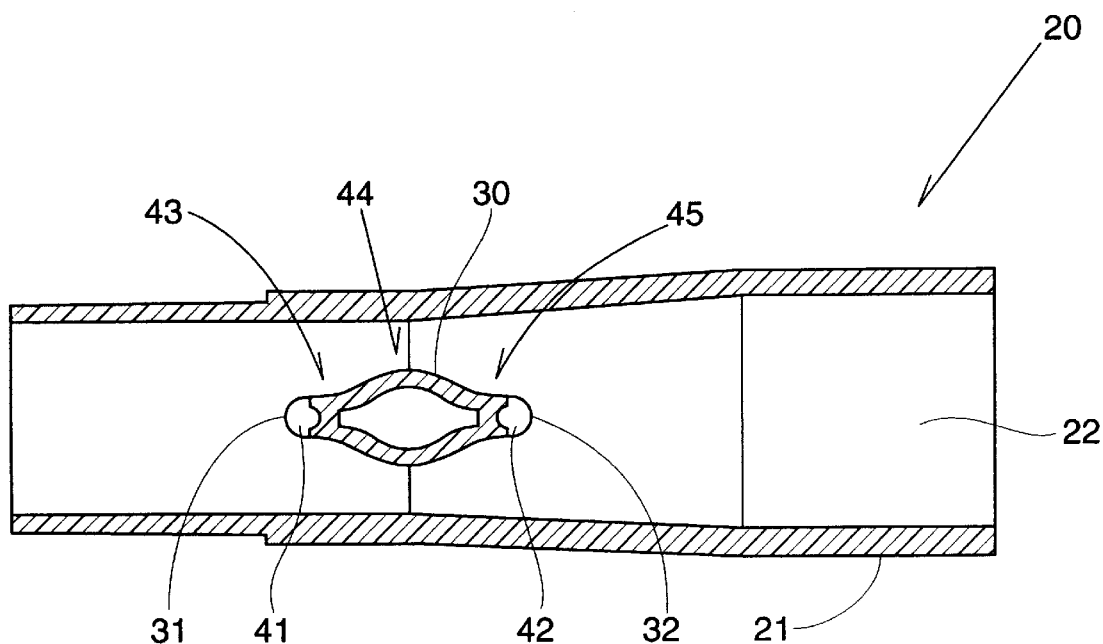
FIG. 2 is a longitudinal sectional view of the flow sensor rotated through 90° from FIG. 1, showing in particular the horizontal cross section of the strut.

The flow sensor 20 utilizes an aerodynamic strut 30 that is disposed within the cylindrical bore 22 of the flow sensor 20 to create a drop in the pressure of the respiration gases flowing through the sensor 20. The strut 30 extends across the entire diameter of the bore 22 of the flow sensor 20 and bisects the circular bore 22 of the sensor 20. As can be seen in FIG. 2, the width of the strut 30 is less than the diameter of the bore 22 and the longitudinal length of the strut 30 is less than the length of the bore 22. Further, the geometric cross section of the strut 30 is symmetrical to the flow of respiratory gases flowing through the sensor 10 either direction.

Referring to FIG. 2, it can be seen that the aerodynamic strut 30 has a longitudinally exposed first edge portion 43, and a second edge portion 45, and a center portion 44 being disposed between the first and second edge portions 43 and 45. The center portion 44 is generally circular in cross section and extends the entire height of the aerodynamic strut 30. The first and second edge portions 43 and 45 are generally trapezoidal in shape with the wider bases of the trapezoids fusing aerodynamically with the generally circular center portion 44 to give the strut 30 a generally elliptical cross section.

The drop in pressure measured by the flow sensor 20 is due to the restriction to flow caused by the presence of the strut 30 within the bore 22 of the sensor 20. The drop in pressure is measured relatively between the first edge 31 of the aerodynamic strut 30 and the second edge 32 of the aerodynamic strut 30. For example, when respiratory gases are flowing through the flow sensor 20 from the first end 23 to the second end 24, a high pressure zone is created immediately adjacent to the first edge 31 of the strut 30 and a low pressure zone is created immediately adjacent to the second edge 32 of the strut 30. The converse is true when the respiratory gases are flowing from the second end 24 of the sensor 20 toward the first end 23 of the sensor. This phenomena is well known.

With reference to FIG. 1, the relative pressures of the respiratory gases flowing through the sensor 20 are collected and conveyed to the wave form analyzing device 50 through lumens 33 and 36. Lumens 33 and 36 are affixed to the outer surface 21 of the body of the flow sensor 20 along a line on the outer surface 21 of the flow sensor 20 that is parallel to the longitudinal axis of the bore 22 of the flow sensor 20. Each of the lumens 33 and 36 are substantially cylindrical and have respective first bores 34 and 37 disposed therein that extend from the outer surface 21 of the flow sensor 20 to the ends 39 and 40 of each lumen 34 and 37, respectively. The first bores 34 and 37 of the lumens 33 and 36 are of sufficient diameter to receive tubing 13, 14 which conducts the collected pressure signals to the pressure transducers 52 and 55.

Communicating with the first bores 34 and 37 are two second bores 35 and 38. The second bores 35 and 38 extend through the body of the flow sensor 20 and into the aerodynamic strut 30. The second bores 35 and 38 are coaxial with the first bores 34 and 37 of lumens 34 and 39 and extend along the entire height of the aerodynamic strut 30 parallel to the first edge 31 and the second edge 32 of the aerodynamic strut 30. In order to permit communication between the interior of the flow sensor 20 and the first bores 34 and 37, each edge 32 and 33 has a respective relieved portion 41 and 42, extending longitudinally into the aerodynamic strut 30 to a depth sufficient to expose a chord of the second bores 35 and 38. The relieved portions 41 and 42 extend substantially the entire height of the aerodynamic strut 30, exposing the chord of the second bores 35 and 38 across substantially the entire diameter of the bore 22 of the flow sensor 20.

In order to transduce the pressure signals output by the flow sensor 20 into usable flow and pressure data, a wave form analyzing device 50 is provided. A basic embodiment of a wave form analyzer device 50 is depicted in FIG. 3. Pressure signals are received at the wave form analyzer 50 via lengths of tubing 13, 14, the exact arrangement thereof to be described below, and transduced into analog voltage signals by differential pressure transducers 52 and 55. Transducer 52 senses the drop in pressure in the respiration gases flowing through the flow sensor 20. As the analog voltage signals output by the transducer 52 are related to the velocity of the flow of respiration gases within the flow sensor 20, the transducer 52 is also known as the flow transducer.

Transducer 55 senses the static pressure of the respiration gases flowing through flow sensor 20. The analog voltage signals output by the transducer 55 may be directly translated into pressure data that will be useful in determining such respiration characteristics as the positive end expiratory pressure (PEEP). The transducer 55 is sometimes referred to as the pressure transducer.

As the output of differential pressure transducers in general are susceptible to changes in the ambient temperature, it is desirable to use a temperature compensated transducer such as the SenSym models SDX05D4 or SSDXL010D, presently manufactured by SenSym, Inc. of Milpitas, Calif. Though it is specifically intended that the basic embodiment of this present invention may be implemented using only temperature compensated transducers, an alternate embodiment of the present invention, illustrated in FIG. 4, incorporates the output of a temperature sensing device 58, which is generally a thermistor, in order to compensate for changes in the ambient temperature that might adversely affect the voltage output of the transducers 52 and 55. However, rather than introducing the additional temperature variable, the preferred mode of implementing the present invention is to augment the inherent temperature compensation abilities of the transducers 52 and 55 through the use of an auto-zero calibration function that will be described in detail below in conjunction with FIG. 5.

Yet another alternate embodiment of the present invention calls for the provision of a third differential pressure transducer (not shown) in the wave form analyzer 50 This third differential pressure transducer is arranged to receive pressure signals from an optional esophageal pressure measuring device of a standard and well known configuration (not shown). Combining the airway pressure signals derived from the esophageal pressure measuring device with the air flow data that is generated from the data gathered from the flow sensor 20, an accurate picture of a person's breathing capabilities can be drawn. The esophageal measurement provides the additional pressure data required for calculating a patient's work of breathing and compliance, two important pieces of information useful in characterizing a patient's pulmonary functions.

As mentioned above, FIG. 3 depicts a very basic embodiment of the tubing structure for connecting the flow sensor 20 to the transducers 52 and 55 of the wave form analyzing device 50. The means for connecting the flow sensor 20 to the transducers 52, 55 of the wave form analyzer comprise a plurality of lengths of plastic tubing 13 and 14. Tubes 13 and 14 connect lumens 33 and 36 to the two ports 53 and 54 of transducer 52, respectively. In order to measure the static pressure within the flow sensor 20, tube 17 is connected between port 56 of transducer 55 and a T-fitting 15 connected in-line with tube 14. Input port 57 of transducer 55 is left open to atmospheric pressures. Furthermore, releasable connector 16 may be provided so that the flow sensor 20 can be disconnected and reconnected from the wave form analyzing device 50. The releasable connector 16 may be any suitable fluidic connector capable of providing a repeatable and secure connection between the severed ends of tubes 13 and 14. The releasable connector 16 facilitates the use of disposable flow sensors 20.

As indicated above, it is preferred to utilize an auto-zero calibration function to compensate for output voltage drift due to temperature variations. It is contemplated that only the flow transducer 52 will be subjected to the auto-zero calibration function. This is because the flow transducer 52 must maintain a sensitivity that is much greater than that of the pressure transducer 55. During the auto-zero calibration, the pressures at the input ports 53 and 54 are equalized and a resulting offset voltage output is measured. Theoretically, this measured offset voltage should match a predetermined offset voltage. But where the output of the transducer 52 has drifted due to temperature changes within the transducer itself or due to some other factor, the measured offset voltage will not equal the predetermined offset voltage. In this case, the magnitude of the difference between the measured and predicted output voltage values will be incorporated into the algorithms that convert the voltage outputs of the flow transducer 52 into useful pulmonary mechanics data. In addition to the auto-zero calibration function, it is also desirable to be able to purge foreign material such as moisture or sputum from the tubes 13 and 14. As the structures for equalizing the pressures between the inputs 53 and 54 of transducer 52 and for purging tubes 13 and 14 are closely associated, they are herein described together.

Figure 5:
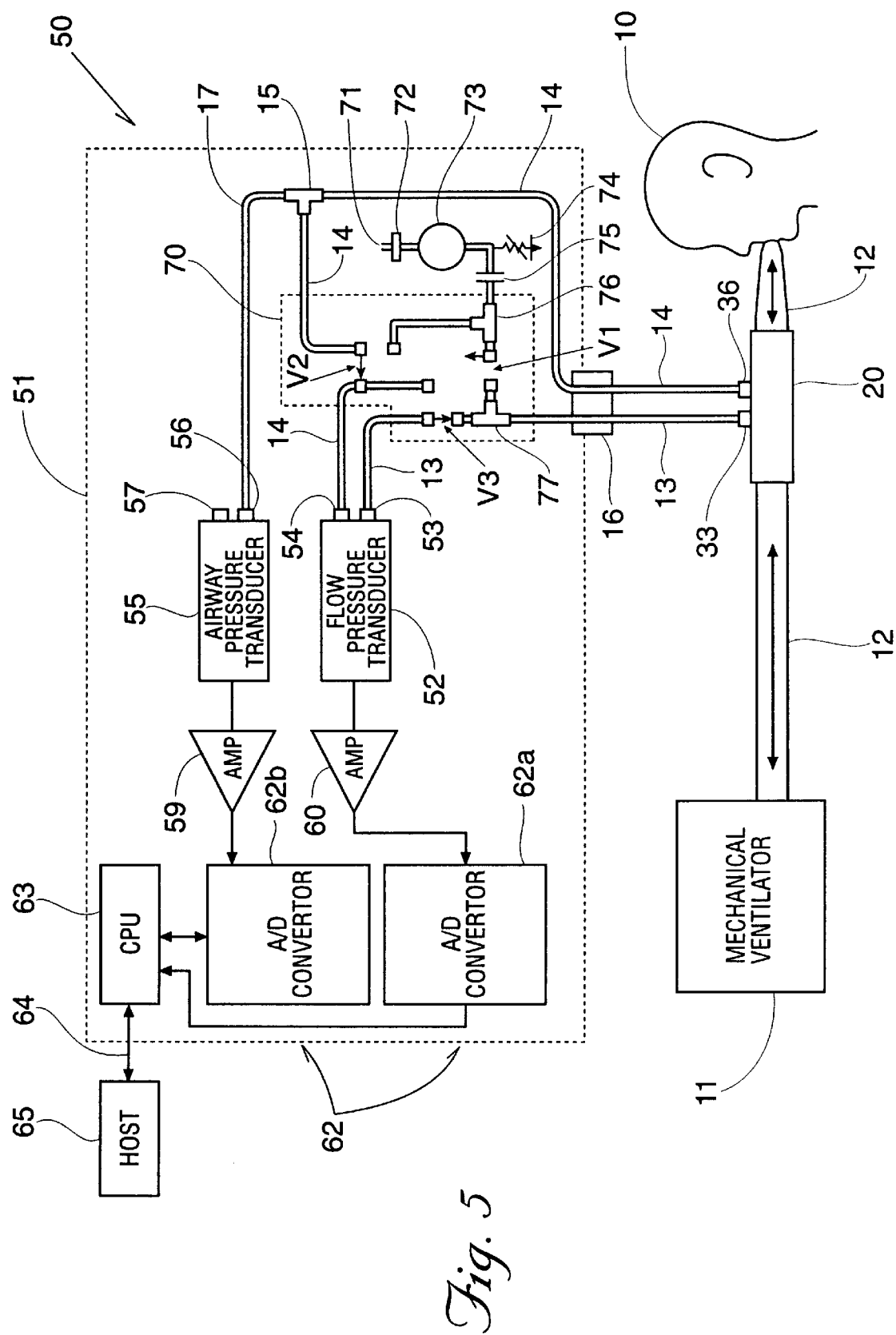
FIG. 5 is a schematic view of the preferred embodiment of the respiratory function monitoring device including the auto-zero and purging structure.
Figure 6A:
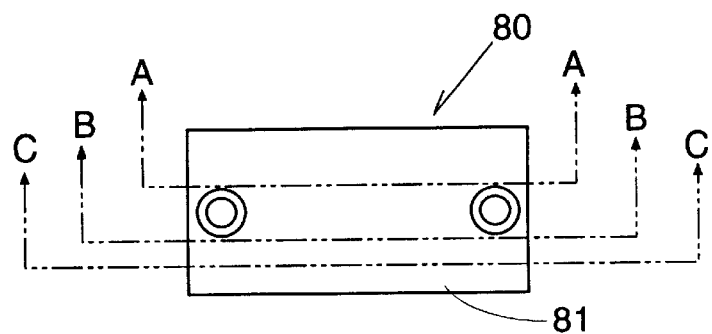
FIG. 6A is a side view of the auto-zero and purging structure as manifested in a solid valve manifold.
Figure 6E:
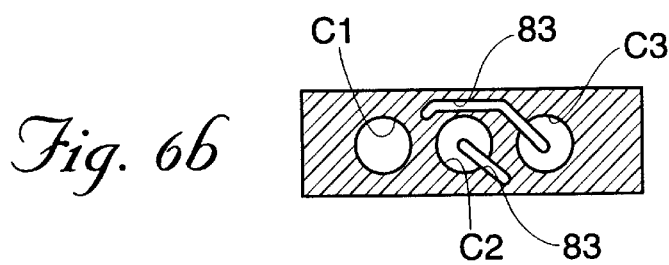
FIG. 6E is a plan view of the valve manifold.
Figure 6E:
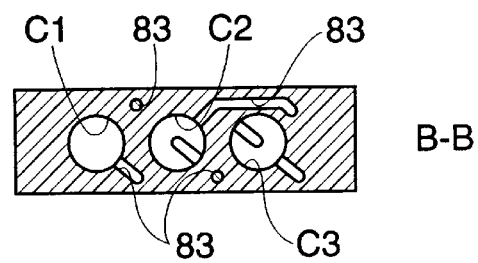
Figure 6E:
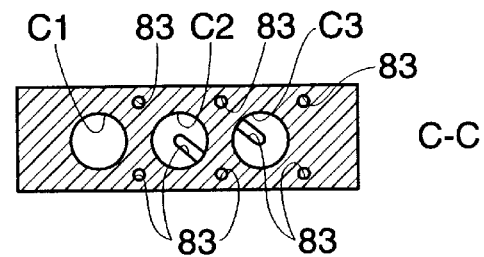
Figure 6E:
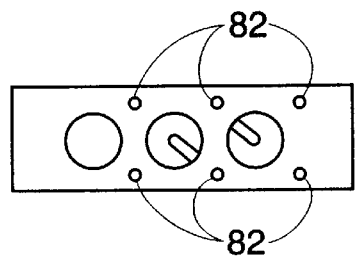

FIG. 5 illustrates the preferred embodiment of the present invention. It will also be observed that the auto-zero and purging system 70 may comprise an air pump 73 having an inlet 71, an air filter 72 interconnected between the inlet 71 and the air pump 73, a needle valve 74 for adjusting the pressure of the air to be used in the purging process, an air tank 75 for maintaining the pressure of the air to be used in the purge process, and three solenoid controlled three-way air valves V1, V2, and V3. These elements, when properly connected, are capable of alternately purging the tubes 13 and 14 and of equalizing the pressure across the input ports 53 and 54 of transducer 52. Though the air tank 75 and needle valve 74 are described as part of the preferred embodiment, it is contemplated that these elements may be omitted without adversely affecting the function of the auto-zero and purging system 70.

In the preferred embodiment of the auto-zero and purging system 70, air tube 14 connects lumen 37 of flow sensor 20 to input port 54 of transducer 52 through solenoid valve V2. Fitting 15 provides communication of pressures from tube 14 through tube 17 to input port 56 of transducer 55 to permit the pressure transducer 55 to sense and report the airway pressure within the flow sensor 20. Tube 13 connects lumen 34 of the flow sensor 20 to input port 53 of the flow transducer 52 through solenoid valve V3 and T-fitting 77. The air pump 73 is connected to solenoid valves V1 and V3 through T-fitting 76. Solenoid valve V1 is in turn connected to tube 13 through T-fitting 77 at a position upstream from solenoid valve V3. In addition, solenoid valve V2 is connected to solenoid V3.

During normal operation, solenoid valves V2 and V3 are in a first position that permits the free communication of pressure signals from the flow sensor 20 to the flow transducer 52 through tubes 13 and 14. At the same time, solenoid V1 is in a first, open position that prevents connection of the air pump 73 to tube 13. In order to equalize pressure across the inputs 53 and 54 of transducer 52, solenoid valve V2 is actuated to disconnect tube 14 from input 54 and solenoid valve V3 is actuated to connect input 53 with input 54. In this state, the flow transducer 52 is pneumatically isolated from the flow sensor 20 and the air pump 73. Solenoid valve V1 remains in its first open state. Actuation signals for the valves V1, V2, and V3 are provided by the central processing unit 63 in accordance with the auto-zero function algorithm described below.

It is preferred to purge tubes 13 and 14 on a one-at-a-time basis, though they can be purged simultaneously. To purge tube 13, solenoid V3 is actuated to isolate input port 53 from the rest of tube 13 and from flow sensor 20. Solenoid V1 is then actuated to connect tube 13 to the air pump 73. Further, solenoid V2 remains in its first position so that the air pump 73 will not be connected to tube 14. Air pump 73 is then activated and air is pumped through tube 13 and into the flow sensor 20. The air pump 73 forces sufficient air at sufficient pressures to force any moisture, sputum, or other blockages that might exist in tube 13, out of the tube 13 and back into the flow sensor 20 where they will not interfere with the communication of pressure signals to the flow transducer 52. The air pump 73 will operate for a predetermined length of time after which it will be deactivated. Upon deactivation of the air pump 73, valves V3, V1, and V2 are all actuated in order to reconnect input port 53 to tube 13, disconnect the air pump 73 from tube 13, and connect the air pump 73 to tube 14, respectively. Once this has been accomplished, the air pump 73 is reactivated and air is pumped through tube 14 into the flow sensor 20 in order to force any foreign materials out of the tube 14 and into the flow sensor 20. After operating for a predetermined length of time, the air pump 73 is again deactivated and solenoid V2 is actuated to reconnect input port 54 to tube 14 and to the flow sensor 20. FIGS. 6A–6E depict an alternate embodiment of the auto-zero and purging system 70. This alternate embodiment is functionally equivalent to the auto-zero and purging system 70 depicted in FIG. 5. In this alternate embodiment, the tubing that interconnects the solenoid valves V1, V2, and V3 and the valves themselves are replaced with a solid valve manifold 80. The valve manifold 80 is comprised of a solid block of a medical grade plastic or other suitable material. The body 81 of the manifold 80 is provided with a number of tubing ports 82 and with three cavities, C1–C3, arranged to receive the solenoid valves V1, V2, and V3, respectively. The ports 82 communicate through a plurality of channels 83 with the cavities C1–C3, and subsequently, with the solenoid valves V1, V2, and V3, in the same manner as described in conjunction with the embodiment illustrated in FIG. 5. The valve manifold 80 reduces the amount of space required upon the circuit board 51 of wave form analyzer 50 for the auto-zero and purging system 70. It is also believed that failures due to kinks in the tubes used in the auto-zero and purging system 70 can be minimized by using the valve manifold 80 depicted in FIGS. 6A–6E.

The algorithms that control the auto-zero and purging system 70 are implemented by a central processing unit 63 that is resident within the wave form analyzer 50. The algorithms will be described below in conjunction with the description of the algorithms that convert the output of the transducers 52 and 55 into useful pulmonary mechanics data.

Referring again to FIGS. 3–5, transducers 52 and 55 are electrically connected to amplifiers 59 and 60, respectively. A suitable amplifier is presently manufactured by Analog Devices, of Norwood, Mass., and is designated as model AD620. The voltage signals received by the amplifiers 59 and 60 from the respective transducers 52 and 55, are amplified and transferred to an analog-to-digital converter means 62.

Figure 4:
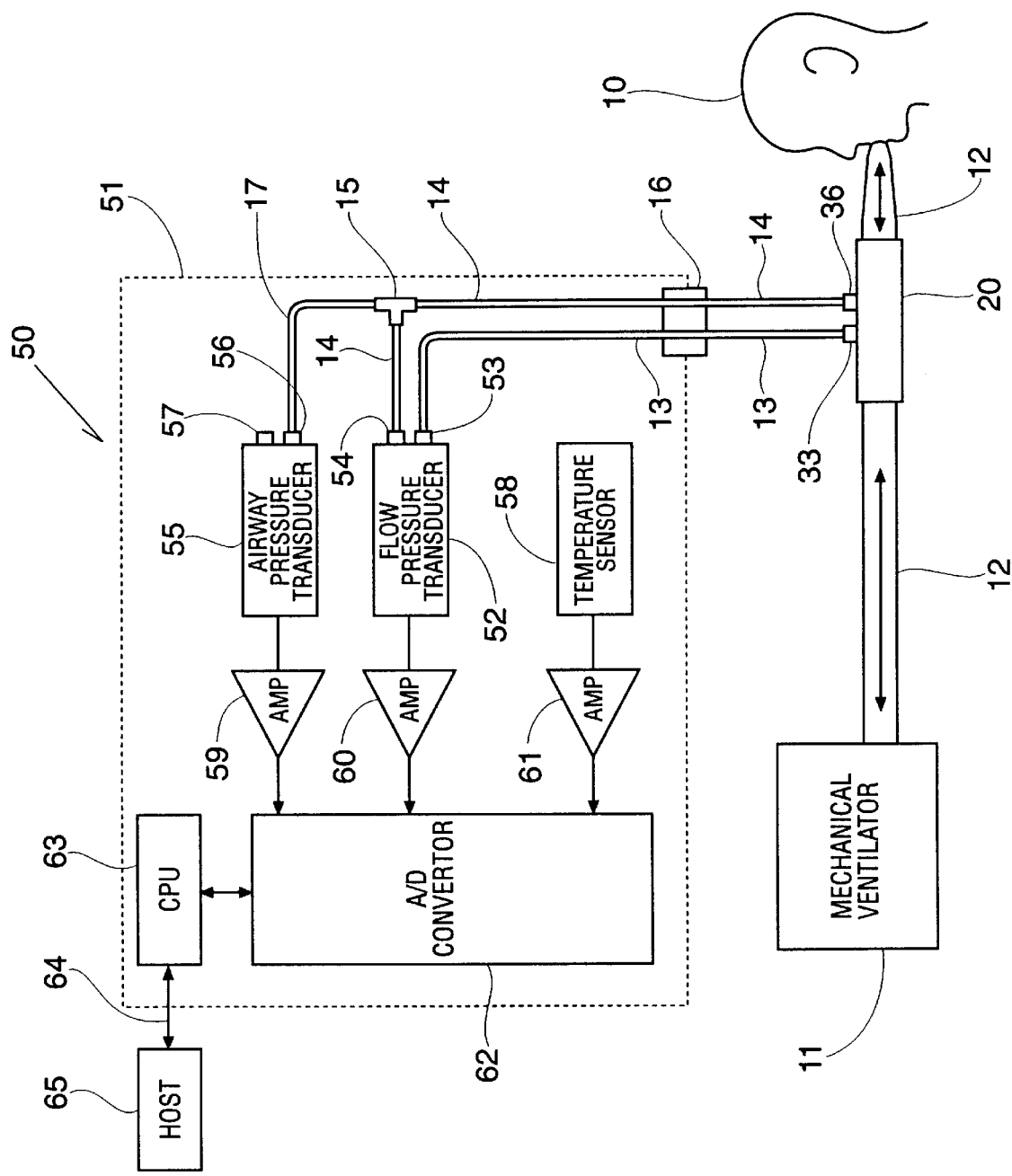
FIG. 4 is a schematic view of an alternate embodiment of the respiratory function monitoring device including a temperature indicating means.

FIGS. 3 and 4 depict embodiments of a the waveform analyzer 50 that have a single analog-to-digital converter means 62. However, the preferred embodiment of the analog-to-digital converter means 62 illustrated in FIG. 5 comprises two separate analog-to-digital converters, 62A and 62B. In any of the embodiments of FIGS. 3, 4, and 5, the analog-to-digital converter means 62 must have at least two input channels, one for each transducer 52 and 55. However it is preferred that the analog-to-digital converter means 62 have at least four inputs so that additional components such as an additional transducer or a thermistor 58 can be added to the wave form analyzing device 50. Further, in order to solve the problem of quantization errors in the conversion of the analog voltage values into digital voltage values, the analog-to-digital converter means 62 must have at least one analog-to-digital converter having 19-bit useful resolution. In the embodiments of FIGS. 3 and 4, the analog-to-digital converter means 62 ideally should have at least four input channels and a useful resolution of at least 19 bits. Alternatively, the preferred embodiment of FIG. 5 utilizes a high resolution analog-to-digital converter 62A to convert the analog voltage output by the flow transducer 52 and a lower resolution analog-to-digital converter 62B to convert the analog voltage output by the pressure transducer 55 and possibly a temperature sensing means 58, or a third transducer (not shown). Where the analog-to-digital converter means 62 comprise a high and a low resolution analog-to-digital converters 62A and 62B, only the high resolution analog-to-digital converter 62A need have at least 19-bits useful resolution. The low resolution analog-to-digital converter 62B may have a lower resolution of around 12-bits useful resolution. It is believed that by providing at least 19-bit analog-to-digital conversion resolution for at least the flow transducer 52, the need for complex amplifying systems is obviated. An analog-to-digital converter considered appropriate for use with the analog-to-digital converter means 62 of this application is the 24-bit nominal resolution ADS1210 analog-to-digital converter presently manufactured by Burr-Brown, Inc. of Tucson, Ariz. Another analog-to-digital converter considered appropriate for this application is the 12-bit resolution LTC1598 analog-to-digital converter that is presently manufactured by Linear Technologies, Inc. of Milpitas Calif.

A central processing unit 63 receives the digital output of the analog-to-digital converter means 62. As described above, the configuration of the central processing unit 63 is of a type well known in the art. In this instance the central processing unit 63 is comprised of a microprocessor (not shown) that operates in conjunction with a read only memory (ROM) means (not shown) and a random access memory (RAM) means. One suitable microprocessor that may be used with the central processing unit 63 of the present invention is an Intel model 80C251SB presently manufactured by Intel Corporation of Santa Clara, Calif. The central processing unit 63 processes the digital data received from the analog-to-digital converter means 62 according to a program stored therein. Useful pulmonary mechanics data produced by the central processing unit 63 is communicated to a host system 65 via an input/output means 64. The input/output means 64 may comprise any number of devices or structures for communicating digital data, but in the present invention, the input/output means 64 is comprised of a serial I/O port that is connected to a complementary serial I/O port of the host system 65. The host system 65 provides power to the wave form analyzing device 50 and also provides means for displaying the pulmonary mechanics data.

Though the flow and pressure data that is output to the host system 65 is useful in itself, it is generally desirable to use this data to calculate more pulmonary function indicators so as to gain a more complete understanding of the patient's pulmonary functions. These indicators may be calculated by the central processing unit 63 of the wave form analyzing device 50 or by a central processing unit of the host system 65. Furthermore, the means for displaying the pulmonary mechanics indicators provided to, or calculated by, the host system 65 may take the form of a numerical display, capable of displaying only the numerical values of the indicators, or a high resolution monitor that is capable of reproducing graphical as well as numerical versions of the pulmonary mechanics indicators.

In order to convert the pressure signals produced by the flow sensor 20 into useful pulmonary mechanics data, the performance of the flow sensor 20, in relation to the voltage output of the transducers 52 and 55 must be characterized. In general, it is known that the drop in pressure across an obstruction in an airway is related to the square of the velocity of the fluids flowing through the airway. This is also true for the differential pressure flow sensor 20. The general relationship between the flow velocity and the pressure drop as measured across the strut 30 by the transducer 52 is given by:

$$\text{Flow velocity}^2 \, \Delta P$$

where $\Delta P$ is the drop in pressure across the strut 30 of the flow sensor 20. This relationship is unique for every unique flow sensor geometry and must be derived empirically. Accordingly, the flow sensors 10 that are to be used with the wave form analyzer 50 are manufactured from the same molds so that the geometric variation in each flow sensor 20 is negligible.

Determining the flow to pressure drop relationship is accomplished by forcing air through the flow sensor 20 at predetermined flow rates and measuring the resulting drops in pressure across the strut 30 through the lumens 33 and 36 to generate a set of data points. A second order linear equation is then fit to the data points. This equation has the same general form as given above. Using this equation a flow velocity for gases flowing through the flow sensor 20 can be calculated from the differential pressure measured across the strut 30.

To calibrate the transducers 52 and 55 of the wave form analyzer 50, a more involved method is required. The method herein described for calibrating the wave form analyzer 50 is given in general terms only, as it is to be understood that the pressures and temperatures disclosed could be modified without straying from this method. To begin, the wave form analyzer 50 is connected to a calibration device (not shown) that may be a computer calibrating device. The wave form analyzer 50 is powered up and permitted to stabilize at approximately 25° Celsius. A pressure source (not shown) is simultaneously connected to each port 53 and 54 of transducer 52 and to a manometer (not shown), and a pressure of approximately 53 inches H$_2$O is applied. In this arrangement, the pressure present upon the input ports 53 and 142 of transducer 52 are the same. The exact pressure is read out on the manometer and the voltage output by the transducer 52 is also measured and recorded. Once the voltage output from transducer 52 has been recorded, the pressure applied across the input ports 53 and 54 is permitted to drop to zero as measured by the manometer. The voltage output by the transducer 52 corresponding to the zero pressure applied across the input ports 53 and 54 is also recorded. Next, the pressure source is removed from input port 54 and a small amount of pressure, approximately ten inches H$_2$O, is applied to input port 53 to approximate a differential pressure. The pressure applied to input port 53 is measured using the manometer, and the voltage output by the transducer 52 corresponding to this pressure is also recorded. Finally, the pressure source is removed from input port 53 and is reconnected to input 54. A small pressure, approximately ten inches H$_2$O, is applied to input port 54 to again approximate a differential pressure. The pressure applied to port 54 is measured using the manometer and is recorded along with the voltage output corresponding to this pressure. By comparing the known pressures that were applied to the transducer 52, measured using the manometer, with the voltages output by the transducer 52, the response of the transducer 52 to various input pressures can be characterized. This same calibration technique may be utilized with transducer 55.

As mentioned above, one alternative embodiment of the wave form analyzer 50, illustrated in FIG. 4, utilizes a thermistor 58 to compensate for variations in the temperature of the transducers 52 and 55 mounted upon the wave form analyzer 50. Use of the thermistor 58, necessitates an additional calibration step for the wave form analyzer 50. In this additional step, the above described calibration method is carried out an elevated temperature approximately 10 to 12° Celsius higher than the initial temperature at which the wave form analyzer 50 transducers were calibrated. It is important that the temperatures of the initial calibration step, and the second calibration step be measured. Utilizing the data recorded in the first and second calibration steps, it is possible to characterize the response of the transducers 52 and 55 with respect to both pressure and temperature.

Figure 7:
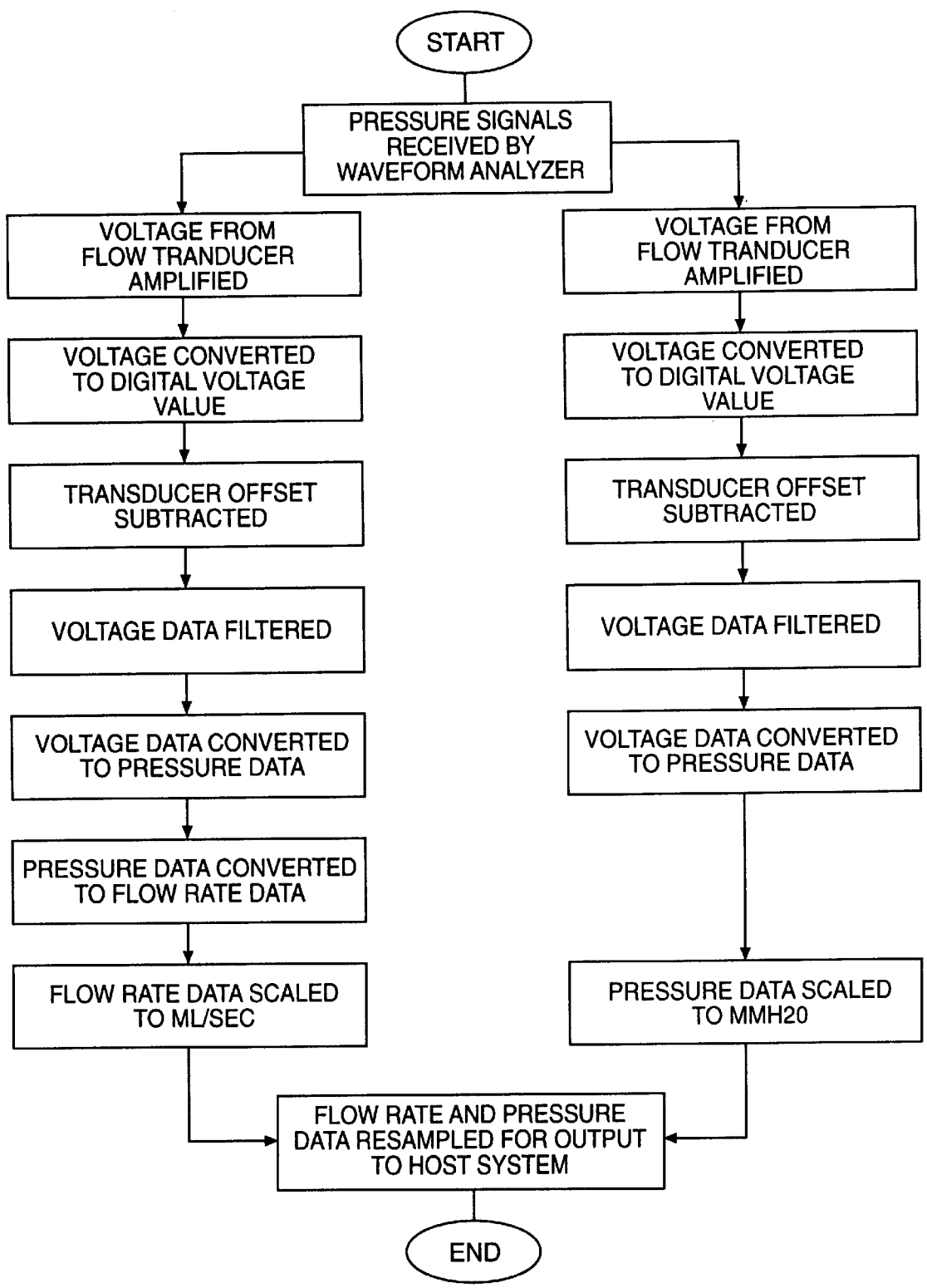
FIG. 7 is a flowchart outlining the method whereby pressure signals from the flow sensor are converted into useful pulmonary mechanics data.

The algorithm for converting pressure signals output by the flow sensor 20 of FIGS. 3 and 5 into useful pulmonary mechanics data, is herein described in conjunction with FIG. 7. The conversion process begins when pressure signals from the flow sensor 20 are received at the wave form analyzer 50 by transducers 52 and 55. Transducers 52 and 55 output voltage signals that are subsequently converted into gas flow rate and static pressure values, respectively. The voltages from the transducers 52 and 55 are amplified by respective amplifiers 59 and 60. These amplified analog voltage signals are transferred to the analog-to-digital converter means 62 which, using a well know over-sampling technique, converts the analog voltage signals from transducers 52 and 55 into digital voltage values which are output at a rate of approximately one hundred samples per second to the central processing unit 63. In the central processing unit 63, a transducer offset voltage is subtracted from each of the voltage values derived from the transducers 52 and 55. The transducer offset voltage is simply that voltage at which the transducers 52 and 55 are normally maintained. It is from the magnitude of the variation from this transducer offset voltage that useful information is derived. The voltage data derived from the transducers 52 and 55 are next filtered using standard low pass software filtering techniques.

The next manipulation of the voltage data derived from the transducers 52 and 55 involves the use of the previously derived characterization equations derived for the transducers 52 and 55 during the calibration process described above. Using these characterization equations, the filtered voltage values derived from the transducers 52 and 55 are converted into digital pressure values. Next, utilizing the second order equation that characterizes the pressure drops across the strut 30 of the flow sensor 20 for varying gas flow rates, the pressure value derived from transducer 52 is then converted into a flow rate value. The flow rate data and the pressure data, respectively derived from transducers 52 and 55, are then scaled, the flow rate data to a scale of milliliters per second, and the pressure data to a scale of millimeters H$_2$O. The flow rate and pressure data are then re-sampled for output to the host system. Data is output to the host system at a rate that can be set at anywhere between 20 Hz and 100 Hz.

Figure 8:
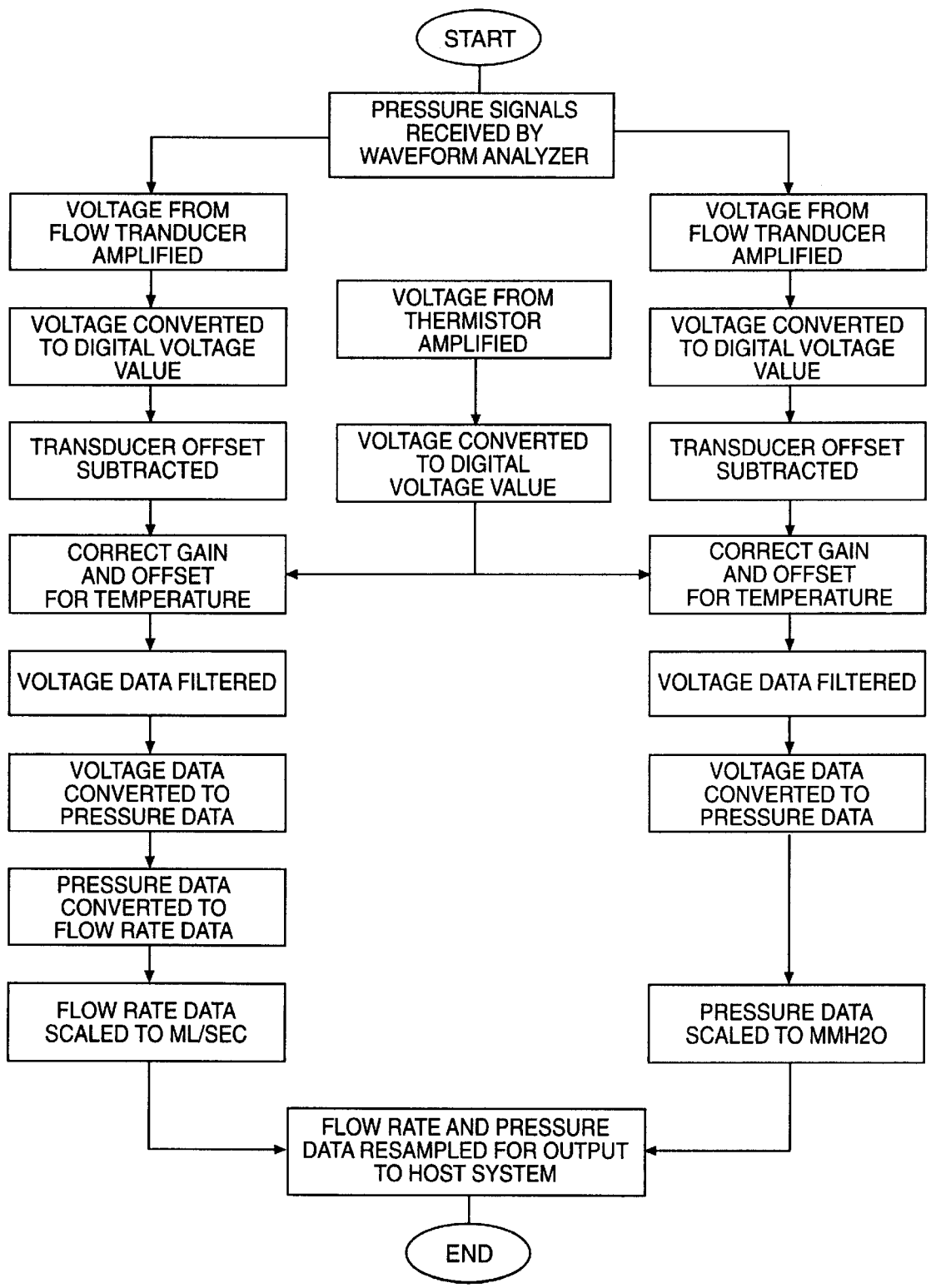
FIG. 8 is a flowchart outlining the method whereby the embodiment illustrated in FIG. 4 converts pressure signals from the flow sensor into useful pulmonary mechanics data in such as manner as to compensate for variations of temperature.

Referring now to FIGS. 4 and 8, the alternate embodiment which utilizes a thermistor 58 to compensate for temperature variations in the transducers 52 and 55, is herein described. In this alternate embodiment, voltage values from the flow transducer 52 and the pressure transducer 55 are amplified, converted to digital voltage values, and have their transducer offset voltages subtracted therefrom, as described in conjunction with FIG. 7. However, as can be seen in FIG. 8, there is an additional voltage value that is derived from the thermistor 58. This voltage value is amplified, converted to a digital voltage value, has its thermistor offset subtracted, and is filtered prior to being utilized to compensate the voltage values derived from the flow transducer 52 and the pressure transducer 55. Though the voltage data derived from the thermistor 58 is itself filtered using a low pass filtering technique, the temperature compensation of the voltage values derived from the transducers 52 and 55 takes place before those voltage values are filtered themselves. The temperature compensation characterization equations that were derived in the two-step calibration method described above are utilized to calculate a corrected voltage value for each of the voltage values derived from the transducers 52 and 55. The corrected flow and pressure voltage values are then filtered, and converted into flow rate and pressure data as described in conjunction with FIG. 8.

Rather than rely on the inherent temperature compensating capabilities of the transducers 52 and 55, or upon the use of a thermistor 58 as illustrated in FIGS. 4 and 9, the preferred embodiment of the present invention as illustrated in FIGS. 5 and 8, utilizes an auto-zero and purging system 70, the physical structure of which was described above. As can be seen from the flow equation set out above, a small amount of drift in the offset voltage can cause a dramatic variance in the reported flow rates. Therefore, it is critical to maintain the offset voltage within its specified tolerances so that the device can perform at the required resolution. Using the auto-zero function, of the present invention, it is possible to counteract drift as needed to maintain the requisite resolution. The auto-zero function involves equalizing the pressure across the flow transducer 52 and measuring the resulting offset voltage.

As was described above, the offset voltage of the flow transducer 52 is measured by actuating solenoid valve V2 to disconnect tube 14 from input 54 and actuating solenoid valve V3 to connect input 53 with input 54, thereby equalizing the pressure present at both input 53 and input 54. The offset voltage is that voltage output by the flow transducer 52 when the pressure has been equalized as between input port 53 and input port 54. The simplest method for incorporating this newly measured offset voltage is to write this offset voltage value to the central processing unit 63, which will store the offset voltage value and use it until a subsequent offset voltage value is recorded and written over the previous offset voltage value. Between each auto-zero function, the offset voltage value most recently recorded is used to convert the voltage signals output by the transducers during normal operation into useful pulmonary mechanics data. This method is termed a reactive auto-zero offset measurement.

It is also contemplated that a predictive auto-zero offset measurement may be performed. Rather than simply using the most recent offset voltage value that has been measured and recorded in the central processing unit 63, a predictive auto-zero offset measurement system predicts future offset voltage values. To accomplish this predictive function, a reactive auto-zero offset measurement algorithm is implemented. However, rather than simply overwriting the previously measured offset voltage value, a predetermined number of offset voltage values are recorded in the central processing unit 63. Once this predetermined number of offset voltage values has been recorded, the offset voltage values are used to characterize a second order or higher equation so as to enable the calculation of future voltage offset values based on the immediate past history of the variation in measured offset voltage values.

As the auto-zero calibration function will necessarily interfere with the normal operation of the wave form analyzer 50, it is also desirable to vary the intervals between each auto-zero calibration function. The length of these intervals will be based upon the magnitude of variation in the offset voltage values themselves. Where the amount of drift in the offset voltage values is small, the interval between each auto-zero calibration can be made longer, and conversely, where the amount of drift in the offset voltage value is great, the intervals between each auto-zero calibration function will be made shorter.

Preferably, the auto-zero calibration function and the purging function do not take place simultaneously. When solenoid valve V3 is actuated to connect input port 53 to input port 54 of flow transducer 52, solenoid valve V2 must also be actuated so as to isolate the flow transducer 52 from the flow sensor 20 and the air pump 73. Therefore, it is necessary to schedule the auto-zero calibration function and the purging function to minimize the interruption to the normal operation of the wave form analyzer 50. Consequently, these functions are scheduled to occur at the end of the expiratory portion of a breath, where the flow and pressure are close to their baseline values. It is preferred that the auto-zero and purge functions be instituted during that period following expiration where the flow of respiration gases through the flow sensor 20 is substantially zero. Where each cycle of respiration is slow and regular, the auto-zero and purge functions can generally be accommodated within the period of substantially zero flow within the flow sensor 20. However, where a patient's respiration becomes faster or irregular, the auto-zero and purge functions will be instituted earlier during the expiratory portion of the breath cycle.

Though it is intended that the auto-zero function and the purging function be instituted at the end of an expiratory portion of a patient's breath, it is to be understood that the auto-zero and purging functions can be instituted on a fixed time basis, i.e. every 30 seconds, every minute, or every 5 minutes, etc. It is also contemplated that the auto-zero and purge functions can be instituted at the same time.

One important variable in the operation of the purge system is the length of time for which the air pump 73 will operate. A first mode requires the pump to operate for approximately 0.5 seconds each time it is activated, pushing typically one cc of air, which is roughly equivalent to eighteen inches to a foot of the tubing used to connect the flow sensor 20 to the wave form analyzer 50. Alternatively, a second mode bases the operation time of the air pump 73 upon the frequency and magnitude of pressure cycles that the flow sensor has been subjected to. A pressure cycle comprises an inspiration and expiration of a patient's breath. During the pressure cycle, moist air or other foreign matter such as sputum, are forced into the tubes 13 and 14 of the flow sensor 20. Each successive pressure cycle or breath pushes a small portion of the moisture farther into the tubes 13 and 14. By requiring that air pump 73 operate so as to create a total net outflow of air when compared with the volume of air and moisture forced into the tubes by the pressure cycles, the user of the wave form analyzer 50 can be assured that all moisture or other foreign matter within the tubes 13 and 14 has been forced out of the tubes and back into the flow sensor 20 where it will not cause degradation of the pressure signals being transmitted to the wave form analyzer 50.

In the event that a blockage of the tubes 13 and 14 should occur between purging functions, the central processing unit 63 is capable of recognizing and remedying the blockage. Generally speaking, a blocked tube results in flow rate data which is both much larger than the actual flow rate and which is asymmetrical in that inspired and expired volumes are very different. Further, the static pressure data will be, on the other hand, almost undisturbed by the blockage. When the central processing unit detects such a state, the purging function will be immediately instituted.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A respiratory function monitoring device comprising:
   a flow sensing device in fluidic communication with a first and a second pressure transducer, the first pressure transducer arranged to measure a differential pressure corresponding to a gas flow rate, the second pressure transducer arranged to measure a static pressure;
   amplifying means electrically connected to the first and second pressure transducers, the amplifying means for amplifying voltage signals output by the pressure transducers;
   an analog to digital converter for translating the analog voltage valves derived from the first and second pressure transducers;
   a central processing unit arranged to communicate with the analog to digital converter, the central processing unit being capable of executing a program, the program being designed to convert the digital voltage values from the first pressure transducer into flow rate data and the voltage values from the second pressure transducer into pressure data; and
   an input/output means for communicating the flow rate and pressure data to a host system wherein the flow sensing device comprises a hollow cylindrical body having a bore with a first end and a second end, the first and second ends arranged for connection between a ventilator and a patient;
   a strut disposed within the bore of the body across the entire diameter of the bore and parallel to the axis of symmetry of the bore, the strut having symmetrical end portions flowing aerodynamically from a center portion, the symmetrical end portions each having a leading edge with a groove formed therein.

2. The respiratory function monitor of claim 1 wherein the flow sensing device comprises:
   a pair of lumens coupled to an outer surface of the body of the flow sensing device, each lumen communicating with a respective groove so as to permit the measurement, across the strut, of a differential pressure of a gas flowing through the flow sensing device.

3. The respiratory function monitor of claim 2 wherein the respective grooves of the flow sensing device extend across substantially the entire height of the strut.

4. The respiratory function monitoring device of claim 1 wherein the conversion device further comprises:
   a third transducer arranged to receive pressure signals from an esophageal pressure sensing device, the voltage signals of the third transducer being amplified by the amplifying means, the amplified analog voltage signals derived from the third transducer being translated by the analog to digital converter into digital voltage data, the digital voltage data being processed by the central processing unit into pressure data that is transferred to the host system.

5. The respiratory function monitoring device of claim 1 wherein the conversion device further comprises:
   a temperature indicating means arranged so as to give the temperature of the conversion device.

6. The respiratory function monitoring device of claim 1 wherein the analog to digital converter of the conversion device has at least four input channels.

7. The respiratory function monitoring device of claim 1 wherein the conversion device further comprises a purge system, the purge system comprising:
   a first valve means;
   a second valve means;
   a third valve means;
   an air pump having an inlet and an outlet, the outlet of the air pump being coupled by a first and second fluidic connection means to the first valve means and the second valve means, respectively;
   the third valve means coupled to a first lumen via a third fluidic connection means and to a first input port of a flow transducer via a fourth fluidic connection means, the third valve means selectively permitting communication between the first lumen and the first input port;
   the second valve means being also coupled to a second lumen through a fifth fluidic connection means and to a second input port via a sixth fluidic connection means;
   the first valve means being also coupled by a seventh fluidic connection means to the third fluidic connection means adjacent the third valve means between the third valve means and the first lumen;
   an eighth fluidic connection means being coupled between the second and third valve means such that the second and third valve means may selectively permit communication between the first input port and the second input port.

8. The purge system of claim 7 wherein the valve means comprise a solenoid activated three-way air valve.

9. The purge system of claim 7 wherein the fluidic connection means are comprised of discrete tubes.

10. The purge system of claim 7 wherein the fluid connection means comprise channels formed within a solid valve manifold, the solid valve manifold being further arranged to receive the valve means.

11. A respiratory function monitoring device comprising:
    a flow sensing device having a hollow cylindrical body with a bore and a first end and a second end, the first and second ends arranged for connection between a ventilator and a patient;
    a strut disposed within the bore of the body of the flow sensing device, the strut having symmetrical end portions flowing aerodynamically from a center portion, the symmetrical end portions each having a leading edge with a groove formed therein, the respective grooves extending across substantially the entire height of the strut;
    a pair of lumens coupled to an outer surface of the flow sensing device, each lumen communicating with a respective groove so as to permit the measurement of a differential pressure of a gas flowing through the flow sensing device;
    the flow sensing device being in fluidic communication via the pair of lumens with a pair of differential pressure transducers, a first of the pair of transducers arranged to measure a differential pressure corresponding to a gas flow rate a second of the pair of transducers arranged to measure a static pressure;

amplifying means for amplifying voltage signals output by the transducers;

an analog to digital converter for translating the analog voltage valves derived from the transducers;

a central processing unit arranged to communicate with the analog to digital converter, the central processing unit being capable of executing a program, the program being designed to convert the digital voltage values from the first transducer into flow rate data and the voltage values from the second transducer into pressure data; and an input/output means for communicating flow rate and pressure data to a host system.

* * * * *